United States Patent [19]
Altadonna

[11] Patent Number: 5,853,768
[45] Date of Patent: Dec. 29, 1998

[54] TOPICAL PREPARATION AND METHOD FOR PAIN RELIEF

[76] Inventor: James Altadonna, 90 E. 2nd St., Deer Park, N.Y. 11729

[21] Appl. No.: 811,276

[22] Filed: Mar. 4, 1997

Related U.S. Application Data

[63] Continuation of Ser. No. 399,105, Mar. 1, 1995, abandoned.

[51] Int. Cl.$^6$ ..................................................... A61K 33/36
[52] U.S. Cl. ........................... 424/667; 514/692; 514/729; 514/667; 514/817
[58] Field of Search ............................. 424/667; 54/729, 54/692, 817

[56] References Cited

U.S. PATENT DOCUMENTS

| | | | |
|---|---|---|---|
| 4,564,521 | 1/1986 | Altadonna | 424/150 |
| 4,731,200 | 3/1988 | Lang | 512/5 |
| 4,762,842 | 8/1988 | Edwards et al. | 514/336 |
| 4,767,847 | 8/1988 | Edwards | 514/336 |
| 4,987,243 | 1/1991 | Kawam et al. | 556/27 |
| 5,013,726 | 5/1991 | Ivy | 514/159 |
| 5,124,320 | 6/1992 | Ivy | 514/159 |
| 5,144,081 | 9/1992 | Heywang | 568/326 |
| 5,175,152 | 12/1992 | Singh | 514/162 |
| 5,252,604 | 10/1993 | Nagy | 514/559 |
| 5,322,683 | 6/1994 | Mackles | 424/45 |

OTHER PUBLICATIONS

Pfizer "Let Us Help You Find Relief That's Right For You" 1997 7 page Internet advertisement for Bengay® relief cream, showing menthol and camphor or menthol as active ingredients.

Universal Merchants, Inc. EEZ–Away 1996 1 page photograph of bottle label for pain relief product having menthol. Note this product also includes iodine.

Comfort Zone 1991 Package label for pain relief product with menthol and potassium iodide, iodine but not camphor.

Richfield Corp "Noah's Relief" 1989 Package label for licensed veterinary pain relief of U.S. Patent No. 4,564,521 with menthol, iodine, and potassium iodide, but not camphor.

Olsen Laboratories, Inc. "For Arthritis Only" 1990 Package label for licensed arthritis product of U.S. Patent No. 4,564,521 with menthol and iodine and potassium iodide, but not camphor.

Olsen Laboratories, Inc. "For Athletes Only" 1990 Package label for licensed arthritis product of U.S. Patent No. 4,564,521 with menthol and iodine and potassium iodide, but not camphor.

Chattem, Inc. "Flexall 454" 1996 Package label for topical pain relief product including menthol.

Mechanical Servants, Inc. "Asorbine Jr" 1998 Package label for topical pain relief antiseptic liniment with menthol, potassium iodide and iodine but not camphor.

Handbook of Pharmaceutical Excipients, p. 189.

*Primary Examiner*—Keith D. MacMillian
*Attorney, Agent, or Firm*—Alfred M. Walker

[57] ABSTRACT

A topical preparation is provided for pain relief in humans, particularly joint pain, wherein methyl glucose, iodide salts, camphor and menthol are provided together wherein the pain relief features are enhanced by the amphoteric characteristics of the methyl glucose and iodide salts enhance penetration of the pain relief components of the composition.

2 Claims, No Drawings

TOPICAL PREPARATION AND METHOD FOR PAIN RELIEF

This application is a continuation of application Ser. No. 08/399,105, filed Mar. 1, 1995, abandoned.

BACKGROUND

The present invention is related to medication, and more specifically, to a topical preparation and methods of using topical preparations for the relief of discomfort and pain in the joints of humans.

Heretofore many substances have been advertised for use in relieving pain in joints of the human body, such as the elbow, knee, thumb area, ankle, neck, wrist, hand and finger, shoulder, etc. However, these substances may normally work relatively fast but with the drawback that the effects are not very long lasting. A proposal to provide long lasting topical relief has been described in U.S. Pat. No. 4,564,521 of James Altadonna, for a topical preparation for relief and joint pain, wherein the topical preparation includes iodine and sodium iodide. Other prior art topical preparations for joint relief include U.S. Pat. No. 4,731,200 for an aqueous-alcohol composition containing benzylidene-camphor derivatives, U.S. Pat. No. 5,013,726 for a lotion containing methyl salicylate, camphor and menthol, U.S. Pat. No. 5,124,320 for an analgesic lotion containing menthol and camphor, U.S. Pat. No. 5,144,081 for a pharmaceutical composition containing camphor and U.S. Pat. No. 5,175,152 for a composition with methyl salicylate, menthol and camphor.

However, none of the prior art describe the use of methyl glucose, iodine, iodide salts, camphor and menthol together for the relief of joint pain.

One aspect of the invention provides compounds for topical application to an effected area of the various joints of the body for relief of pain.

Another aspect of the present invention comprises methods of treating pain which include the application of novel topical treatments.

Accordingly, it is an object of this invention to provide an effective means for pain relief, particularly in the joints of the human body.

It is a further object of the present invention to provide a pain relief compound with amphoteric penetration features designed to hasten the pain relief and to provide deep, long lasting pain relief.

SUMMARY OF THE INVENTION

In accordance with the above related objects, one aspect of the present invention relates to a topical preparation for joint pain relief in humans, wherein methyl glucose, iodine salts, camphor and menthol are provided together such that the pain relief features are enhanced. It is believed that the particular amphoteric characteristics of the methyl glucose and iodide salts enhance penetration of the pain relief components of the composition.

DETAILED DESCRIPTION

The present invention comprises novel compositions with enhanced effectiveness as a topical preparation useful for pain relief, particularly for relief of pain experienced in joints.

The advantages of the present invention are believed to emanate from the novel composition of complex oleyl ether phosphate, e.g. Oleth 3 phosphate, used in combination in Oleth 10, camphor and other active ingredients including lanolin, methyl glucose, iodine containing substance such as tincture of iodine, suitable solvents and/or carriers such as alcohol and/or water, as well as other minor ingredients such as fragrances.

One preferred embodiment of the present invention comprises a lanolin in an amount of about 1 to 15%, preferably 2 to 10%, most preferably about 6.5 to 8.5%, mineral oil in an amount of 0.1 to 3%, preferably 0.5 to 2%, a methyl glucose in an amount of about 0.1 to 5%, preferably about 1.5 to 4%, most preferably about 2 to 3%, Oleth 3 phosphate in an amount of about 0.01 to 3%, preferably 0.5 to 2%, Oleth 10 in an amount of about 0.1 to 7.5%, preferably about 2 to 6%, most preferably about 4.5 to 6%, tincture of iodine (Iodine, Sodium Iodide, H2O, Alcohol) in an amount of about 1 to 5%, preferably about 2 to 3%, Menthol in an amount of about 0.1 to 2%, preferably about 0.5 to 1.5%, Camphor in an amount of about 0.5 to 5%, most preferably about 1 to 3%, and fragrances such as almond or oil of lemon in an amount of about 0.01 to 2%, preferably about 0.25 to 1%. Suitable solvents and/or carriers include alcohol and de-ionized water. The alcohol is preferably less than 50%, most preferably about 40% with the balance of the composition comprising de-ionized water. While this preferred composition comprises lanolin and methyl glucose, those skilled in the art will appreciate that it may be more preferable to use substituted compounds such as a PEG (polyethylene glycol) substituted lanolin, for example PEG 75 lanolin, and/or PPG (polypropylene glycol substituted methyl glucose, for example PPG 20 methyl glucose.

Alternatively, a portion of the Oleth 10 can be substituted with crodafos N3 acid. Those skilled in the art will appreciate that the tincture of iodine can also be decolorized if desired, with a compound such as sodium thiosulphate.

One preferred composition of the present invention comprises:

a. PEG 75 lanolin 7–8%
b. Mineral oil 1%
c. PPG 20 methyl glucose 2.75%
d. Oleth 3 phosphate 1%
   (complex oleyl ether phosphate)
e. Oleth 10 5.5%
   (could reduce slightly and add 1% Crodafos N3 acid)
f. Alcohol 38.25%–39.00%
g. Tincture of Iodine—2–3%
   (Iodine, Sodium Iodide, H2O, alcohol)
   (Decolorize with Thiosulphate)
h. Menthol 1–1.25%
i. Camphor 1–3%
j. Fragrances—almond or 0.5%–1%
   oil of lemon
k. Water (de-ionized) balance This composition may be prepared as follows:

1. To a first mixture of de-ionized water is added PEG 75 lanolin, PPG-20 methyl glucose ether, Oleth 3 phosphate and Oleth 10 until dissolved and cooled.
2. The tincture of iodine is prepared separately.
3. Sodium thiosulphate is added to decolorize the tincture of iodine.
4. Alcohol is added to the first mixture.
5. 1% mineral oil and tincture of iodine is added.
6. Menthol and camphor are added.

7. Fragrances, such as almond extract fragrance are added.

8. A menthol assay is carried out to verify its percentage in the composition, and the amount of menthol is adjusted, if necessary.

While it is believed that the fragrance(s) and water are substantially inactive ingredients in the within compound of the present invention, though the other ingredients are active. For example, the alcohol and iodide salts act to increase penetration of the menthol, camphor and iodine. The enhanced penetration and long lasting effectiveness of the present invention is believed to be due to the combined advantageous effects obtained with the Oleth 3 phosphate in conjunction with the Oleth 10 which, as stated above, may be substituted in part with 1% crodafos N3 acid. The combination of the Oleth 3 phosphate and Oleth 10 is deemed particularly desirable when used in combination with the tincture of iodine, menthol and camphor.

In an alternate embodiment, the composition of the present invention comprises:

a. PEG 75 lanolin up to 8% b. Mineral oil up to 1% c. PPG 20 methyl glucose up to 2.75% d. Oleth 3 phosphate up to 1%
 (complex oleyl ether phosphate)

e. Oleth 10 up to 5.5%
 (could reduce slightly and add 1% Crodafos N3 acid)

f. Alcohol up to 60.00% g. Tincture of Iodine—2–3%
 (Iodine, Sodium Iodide, H2O, alcohol)
 (Decolorize with Thiosulphate)

h. Menthol up to 1.25% i. Camphor 1–3% j. Fragrances—almond or up to 1%
 oil of lemon k. Water (de-ionized) balance

According to one preferred method of the present invention, the composition is applied by soaking an absorbent material, such as a cotton ball and applied topically to the effected area several times a day, such as every three hours for conditions such as tennis elbow or pains in a knee, thumb area, ankle, neck, wrist, hand, finger and/or shoulder. The present invention may be applied topically for extended periods, for example, common periods of treatment extends from about 4 to 12 days, without risking any harmful effects. The composition is generally applied four to approximately twelve days.

Unless otherwise noted, all percentages stated herein are by weight.

I claim:

1. A topical preparation composition for the relief of minor pain in humans consisting essentially of:
(materials are listed by weight of the total composition)
 tincture of iodine 1–5%
 camphor 0.5–under 3%
 menthol 0.5–1.5%.

2. A topical preparation composition for the relief of minor pain in humans consisting essentially of:
(materials are listed by weight of the total composition)
 PEG 75 lanolin 8%
 Mineral oil 1%
 PPG 20 methyl glucose 2.75%
 Oleth 3 phosphate 1%
  (complex oleyl ether phosphate)
 Oleth 10 5.5%
 Crodafos N3 acid 1%
 Alcohol 38.25%–39.00%
 Tincture of Iodine 2–3%
 Menthol 1–1.25%
 Camphor 1–under 3%
 Fragrances—almond or 0.0–1%
  oil of lemon
 Water (de-ionized) balance of composition.

* * * * *